(12) United States Patent
Tanabe

(10) Patent No.: US 7,851,485 B2
(45) Date of Patent: Dec. 14, 2010

(54) THERAPEUTIC AGENT FOR NEUROPATHIC PAIN

(75) Inventor: Tsutomu Tanabe, Tokyo (JP)

(73) Assignees: Japan Science and Technology Agency, Saitama (JP); National University Corporation, Tokyo Medical and Dental University, Tokyo (JP)

( * ) Notice: Subject to any disclaimer, the term of this patent is extended or adjusted under 35 U.S.C. 154(b) by 541 days.

(21) Appl. No.: 11/919,239

(22) PCT Filed: Apr. 26, 2006

(86) PCT No.: PCT/JP2006/309182
§ 371 (c)(1),
(2), (4) Date: Oct. 25, 2007

(87) PCT Pub. No.: WO2006/115302
PCT Pub. Date: Nov. 2, 2006

(65) Prior Publication Data
US 2010/0099702 A1    Apr. 22, 2010

(30) Foreign Application Priority Data
Apr. 26, 2005    (JP)    ............... 2005-128025

(51) Int. Cl.
*A61K 31/47* (2006.01)
(52) U.S. Cl. ................................... 514/309
(58) Field of Classification Search .......... 514/307
See application file for complete search history.

(56) References Cited

U.S. PATENT DOCUMENTS

2008/0194620 A1 * 8/2008 Besne et al. ............... 514/307

FOREIGN PATENT DOCUMENTS

| JP | 2002-516279 A | 6/2002 |
|---|---|---|
| WO | WO 99/49316 A2 | 9/1999 |
| WO | WO 99/61024 A2 | 12/1999 |
| WO | WO 00/37086 A1 | 6/2000 |

OTHER PUBLICATIONS

Supplementary European Search Report dated Dec. 7, 2009, in corresponding EP 06732484.2, 8 pages.
Galiegue et al., "The Peripheral Benzodiazepine Receptor: A Promising Therapeutic Drug Target," Current Medicinal Chemistry, 2003, 10:1563-1572.
Hempenstall et al., "Current treatment options in neuropathic pain," Current Opinion in Investigational Drugs, 2002, 3(3):441-448.
Kontinen et al., "Effects of midazolam in the spinal nerve ligation model of neuropathic pain in rats," Pain, 2000, 85:425-431.
Dalbo et al., "Antinociceptive Effects of Peripheral Benzodiazepine Receptors," Pharmacology, 2004, 70(4):188-94.
Database BIOSIS on STN, BIOSIS (Philadelphia, PA, USA), DN: PREV200000147669 & Sloan, J.W. et al., Effect of chronic diazepam (DZ) treatment, and flumazenil (FLU)—and PK 11195 (PK)-induced withdrawal on the pain threshold in femal rats, Society for Neuroscience Abstracts, 1999, vol. 25, No. 1-2, p. 1948 (abstract, two pages).
Karchewski et al., "Axonal injury-dependent induction of the peripheral benzodiazepine receptor in small-diameter adult rat primary sensory neurons," European Journal of Neuroscience, 2004, 20(3):671-83.
Rady et al., "Confluence of Antianalgesic Action of Diverse Agents through Brain Interleukin$_{1\beta}$ in Mice," J. Pharmacol. Exp. Ther., 2001, 299(2):659-665.
Xiao et al., "Identification of gene expression profile of dorsal root ganglion in the rat peripheral axotomy model of neuropathic pain," Proc. Natl. Acad. Sci., Jun. 11, 2002, 99(12):8360-8365.

* cited by examiner

*Primary Examiner*—Raymond J Henley, III
(74) *Attorney, Agent, or Firm*—Foley & Lardner LLP

(57) ABSTRACT

Disclosed is a therapeutic agent for neuropathic pain having an excellent therapeutic effect on neuropathic pain which is a intractable disease. More specifically, disclosed are a therapeutic agent for neuropathic pain which comprises a peripheral benzodiazepine receptor antagonist (particularly PK 11195) as the active ingredient; a pharmaceutical composition for the treatment of neuropathic pain which comprises a peripheral benzodiazepine receptor antagonist as the active ingredient; a method for the treatment of neuropathic pain using a peripheral benzodiazepine receptor antagonist; and others.

4 Claims, 1 Drawing Sheet

THERAPEUTIC AGENT FOR NEUROPATHIC PAIN

CROSS-REFERENCE TO RELATED APPLICATIONS

This application is a National Stage application of PCT/JP2006/309182, filed Apr. 26, 2006, which claims priority from Japanese application JP 2005-128025, filed Apr. 26, 2005.

TECHNICAL FIELD

The present invention relates to a therapeutic agent for neuropathic pain which has an excellent pain suppressing action against neuropathic pain, a method for treating neuropathic pain using such a therapeutic agent, and the like.

BACKGROUND ART

Neuropathic pain is caused by, for example, injury or dysfunction in a peripheral or central nervous system, and is intractable pain for which opioid receptor agonists such as morphine are not sufficiently effective. Disorders with neuropathic pain include disorders that exhibit hyperalgesic or allodynic symptoms, such as postherpetic neuralgia, trigeminal neuralgia, diabetic neuralgia, and persistent postoperative or posttraumatic pain.

Known analgesics that have hitherto been used in conventional drug treatment include centrally acting opioid receptor agonists such as morphine and non-steroidal anti-inflammatory drugs (NSAIDs) such as indomethacin. However, it is known that these analgesics generally have only a small effect on neuropathic pain, and that the effects provided by analgesics which work well for ordinary nociceptive pain (particularly, narcotic analgesics, etc.) are especially small. The inadequate analgesic effect provided by narcotic analgesics on neuropathic pain is regarded as a major characteristic of neuropathic pain. In some cases, the diagnosis of neuropathic pain is carried out using this characteristic.

Various factors are considered to be intricately involved in the onset of neuropathic pain. Conventionally known treatment methods for neuropathic pain include neurosurgical intervention such as nerve blocking and spinal epidural stimulation, and the lumbar intrathecal administration of drugs such as tricyclic antidepressants and baclofen. However, these treatment methods are either not sufficiently effective or have side effects. As an external preparation, capsaicin cream, which depletes the pain-producing substance P released from the nerve endings and thus alleviates pain, has been reported to be effective for postherpetic neuralgia and postmastectomy pain syndrome. However, due in part to the burning pain caused by capsaicin, the use of capsaicin cream has problems in terms of usefulness and safety. As can be seen, neuropathic pain is an intractable disorder for which an effective method of treatment has yet to be established.

Benzodiazepine receptors are classified into central benzodiazepine receptors and peripheral benzodiazepine receptors. Currently, peripheral benzodiazepine receptors (PBR) are recognized to be present in the central nervous system, and have been found to be present at a high density which is equal to, or higher than, the density of the central benzodiazepine receptors (CBR) present in the same region. Recent studies have reported that peripheral benzodiazepine receptors are present in microglia cells in the brain and are increased by psychoneurotic disorders, such as Alzheimer's disease and the like, by which microglia is activated in the brain.

Animal experiments have shown that peripheral benzodiazepine receptors in peripheral tissues such as adrenal cortex and the like are increased by stress or anxiety, but are, conversely, decreased when the stress is repeated (Drugan, R. C. et al.: Pharmacol. Biochem. Behav., 24:1673-1677, 1986). It has been reported that humans provide substantially the same results when examined with platelets (Gavish, M. et al.: Phamacol. Rev., 51:629-650, 1999). Thus, it is considered that a peripheral benzodiazepine receptor is deeply involved in stress. Recently, an increase in the expression level of PBR in ganglion of the posterior root of spinal nerve of a neuropathic pain model rat has been reported (Eur. J. Neurosci. 20:671 (2004)).

PK11195 (1-(2-chlorophenyl)-N-methyl-N-(1-methylpropyl)-3-isoquinolinecarboxyamide) is a compound developed by Rhone Poulenc Santa, and is known as a substance having a specific antagonistic action (antagonist) on peripheral benzodiazepine receptors (PBR). Conventionally, PK11195 is labeled with $^{11}$C, $^{18}$F, $^{123}$I or the like and used for determining the position of PBR in human heart or brain. PK11195 has been reported to be useful for diagnosing brain glioma or Alzheimer's disease when labeled with $^{11}$C. Japanese Patent Application (Published Japanese Translation of PCT International Publication) No. 2002-516279 (patent document 1) describes that PK11195 is a ligand bindable to a peripheral benzodiazepine receptor with high affinity and is useful for treating an inflammatory state of mammals.

Based on the report that the peripheral benzodiazepine receptor is involved in cell proliferation and that the expression thereof in tumor in human asteroid cells is related to tumor grade and proliferation index, Japanese Laid-Open Patent Publication No. 2003-508343 (patent document 2) describes that PK11195 is a composition usable for prophylaxis, diagnosis, recuperation and treatment of cancer as a substance for decreasing or inhibiting the actions of peripheral benzodiazepine receptors (PBR).

However, PK11195, which is a peripheral benzodiazepine receptor (PBR) antagonist, has not been described in any document as being effective for treating neuropathic pain.

DISCLOSURE OF THE INVENTION

As noted above, no pharmaceutical agent effective for treating neuropathic pain is known yet. Hence, such a pharmaceutical agent is desired to be developed. In light of this, it is an object of the present invention to provide a novel therapeutic agent for neuropathic pain which is highly effective against intractable pain such as neuropathic pain.

The present inventors conducted research based on their own unique ideas for achieving this object, and, as a result found that a peripheral benzodiazepine receptor antagonist such as PK11195 exhibits a highly analgesic effect and completed the present invention.

Accordingly, the present invention provides a therapeutic agent for neuropathic pain, a pharmaceutical composition for treating neuropathic pain, a method for treating neuropathic pain and the like as follows.

(1) A therapeutic agent for neuropathic pain, comprising a peripheral benzodiazepine receptor (PBR) antagonist as an active ingredient.

(2) The therapeutic agent for neuropathic pain of (1), wherein the peripheral benzodiazepine receptor antagonist is selected from 1-(2-chlorophenyl)-N-methyl-N-(1-methylpropyl)-3-isoquinolinecarboxyamide; (−)-N,N-dimethyl-2-methyl-3-[4-(2-phenyl)quinolinyl]propaneamide; (+)-N,N-dimethyl-2-methyl-3-[4-(2-phenyl)quinolinyl]propaneamide; 1-(2-fluoro-5-nitrophenyl)-N-methyl-N-(1- methylpropyl)-3-isoquinolinecarboxyamide; 7-chloro-N,N-5-trimethyl-4-oxo-3-phenyl-3,5-dihydro-4H-pyridazino-[4,5-b]indole-1-acetoamide; and pharmaceutically acceptable salts thereof.

(3) The therapeutic agent for neuropathic pain of (1), wherein the peripheral benzodiazepine receptor antagonist is 1-(2-chlorophenyl)-N-methyl-N-(1-methylpropyl)-3-isoquinolinecarboxyamide (PK11195) or a pharmaceutically acceptable salt thereof.

(4) The therapeutic agent for neuropathic pain of any one of (1) through (3), wherein the neuropathic pain is at least one symptom selected from neuropathic pains in postherpetic neuralgia, trigeminal neuralgia, diabetic neuralgia, cancer pain, persistent postoperative or posttraumatic pain, hyperalgia, allodynia, postthoracotomy pain, CRPS, pain associated with multiple sclerosis, AIDS, thalamic pain, paraplegic pain caused by myelopathy, anesthesia dolorosa and phantom limb pain.

(5) A pharmaceutical composition for treating neuropathic pain, comprising a peripheral benzodiazepine receptor antagonist and a pharmaceutically acceptable carrier.

(6) A method for treating neuropathic pain by administering an effective amount of a peripheral benzodiazepine receptor antagonist to a mammal.

(7) Use of a peripheral benzodiazepine receptor antagonist for producing a therapeutic agent for neuropathic pain.

A therapeutic agent for neuropathic pain according to the present invention is effective for the treatment of neuropathic pain which exhibits symptoms such as postherpetic neuralgia, trigeminal neuralgia, diabetic neuralgia, cancer pain, persistent postoperative or posttraumatic pain, hyperalgia, allodynia and the like.

BEST MODE FOR CARRYING OUT THE INVENTION

Figure 1:
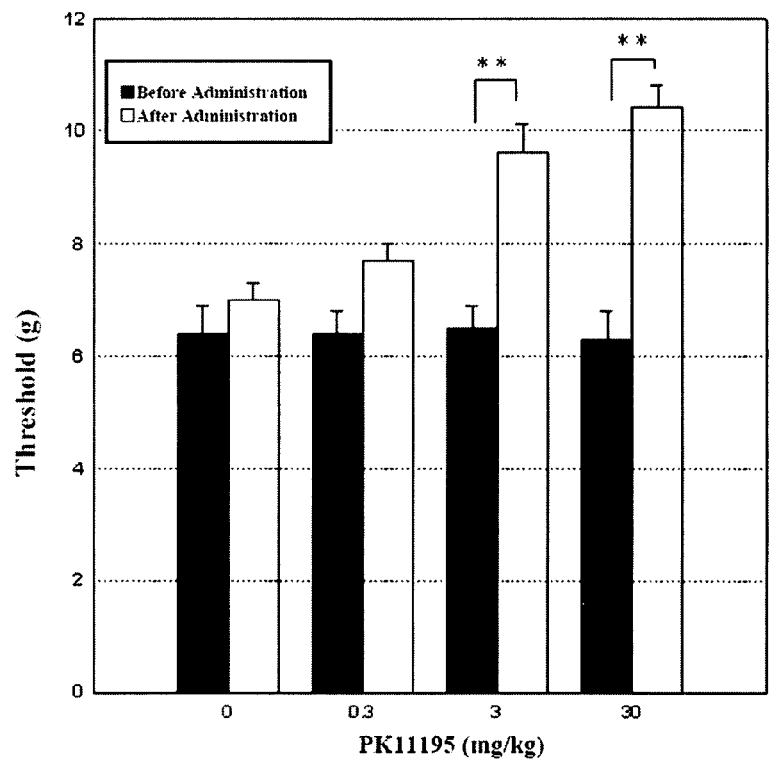
FIG. 1 shows experimental results in Example 1, illustrating a change in the pain threshold against mechanical stimulation exhibited by rats after PK11195 was intraperitoneally administered to the rats having neuropathic pain due to nerve injury.

Hereinafter, the present invention will be described in more detail.

The present invention provides a therapeutic agent for neuropathic pain, comprising a peripheral benzodiazepine receptor (PBR) antagonist as an active ingredient; a pharmaceutical composition for treating neuropathic pain, comprising a peripheral benzodiazepine receptor antagonist and a pharmaceutically acceptable carrier; a method for treating neuropathic pain using a peripheral benzodiazepine receptor antagonist; and the like. Various types of peripheral benzodiazepine receptor antagonists such as PK11195 are known. Surprisingly, the present inventor found that such a peripheral benzodiazepine receptor antagonist, independently, has an effect of treating neuropathic pain for the first time in history. Up until today, there has been no report analyzing the effect of suppressing pain provided independently by a peripheral benzodiazepine receptor antagonist on a neuropathic pain model. For example, recently, an increase in the expression level of PBR in ganglion of the posterior root of spinal nerve of a neuropathic pain model rat has been reported (Eur. J. Neurosci. 20:671 (2004)). However, the authors of this report consider PBS, the expression level of which was increased, as a nerve protecting factor, and presumes that a PBR agonist is clinically more important. This fact proves the originality of the present invention.

As used herein, the term "peripheral benzodiazepine receptor (PBR) antagonist" refers to a substance having an antagonistic action on peripheral benzodiazepine receptors. Benzodiazepine receptors are classified into central benzodiazepine receptors (CBR) and peripheral benzodiazepine receptors (PBR). The peripheral benzodiazepine receptor antagonist used in the present invention has an antagonistic action on peripheral benzodiazepine receptors. The antagonistic action on peripheral benzodiazepine receptors can be confirmed by a known method, for example, a method described in Eur. J. Neurosci. 20:671-683 (2004).

As used herein, the term "therapy" or "treatment" generally means improving the symptoms of humans and mammals other than humans. The term "improvement" refers to alleviating, or preventing exacerbation of, the severity of a disorder as compared with the case where a therapeutic agent of the present invention is not administered. This term also has the meaning of prophylaxis. The term "pharmaceutical composition" refers to a composition containing an active ingredient (PK11195, etc.) useful for the present invention and an additive such as a carrier or the like used in preparing a pharmaceutical agent.

The benzodiazepine receptor (PBR) antagonist used in the present invention is an antagonist specifically boundable to a peripheral benzodiazepine receptor (PBR) which is present in myocardium, lung, adrenal, salivary gland, glial cell and the like at a high density. Examples of the peripheral benzodiazepine receptor (PBR) antagonist usable in the present invention include PK11195 (1-(2-chlorophenyl)-N-methyl-N-(1-methylpropyl)-3-isoquino linecarboxyamide); PK14067 ((−)-N,N-dimethyl-2-methyl-3-[4-(2-phenyl)quinolinyl] propaneamide); PK14068 ((+)-N,N-dimethyl-2-methyl-3-[4-(2-phenyl)quinolinyl]propaneamide); PK14105 (1-(2-fluoro-5-nitrophenyl)-N-methyl-N-(1-methylpropyl)-3-isoquinolinecarboxyamide); SSR180575 (7-chloro-N,N-5-trimethyl-4-oxo-3-phenyl-3,5-dihydro-4H-pyridazino-[4,5-b]indole-1-acetoamide); and pharmaceutically acceptable salts thereof. Among these, a compound especially preferably usable for the present invention is PK11195 (1-(2-chlorophenyl)-N-methyl-N-(1-methylpropyl)-3-isoquinolinecarboxyamide), or a pharmaceutically acceptable salt thereof.

The above-listed compounds are all known and described in documents such as Eur. J. Neurosci. 20:671 (2004), Thrombosis Research 78:293 (1995), Biochem. Biophys. Res. Commun. 310:785 (2003) and the like. PK11195 is available from Sigma-Aldrich, and the chemical structure, physicochemical properties and the like thereof can be checked in the webpage of Sigma-Aldrich (http://www.sigmaaldrich.com/cgi-bin/hsrun/Suite7/Suite/Suite.hjx;start=Suite.HsViewHierarchy.run?Detail=Product&ProductNumber=SIGMA-C0424&VersionSequence=1).

As used herein, the expression "comprising a peripheral benzodiazepine receptor antagonist as an active ingredient" refers to any use as a peripheral benzodiazepine receptor antagonist in any known compound or any pharmaceutically acceptable form of such a compound (for example, in salt, ester, amide, hydrate or solvate state, racemic mixture, optically pure form, prodrug, or the like thereof).

Accordingly, the compound used as an active ingredient in the present invention may be a free compound or a pharmaceutically acceptable salt. Such a "salt" encompasses acid salts and basic salts. Examples of the acid salts include hydrochlorides, hydrobromides, hydroiodides, nitrates, sulfates, bisulfates, phosphates, acid phosphates, acetates, lactates, citrates, acid citrates, tartrates, bitartrates, succinates, maleates, fumarates, gluconates, saccharates, benzoates, methanesulfonates, ethanesulfonates, benzenesulfonates, p-toluenesulfonates, 1,1'-methylene-bis-(2-hydroxy-3-naphthoic acid) salts, and the like. Examples of the basic salts include alkaline metal salts such as sodium salts, potassium salts, and the like; alkaline earth metal salts such as calcium salts, magnesium salts and the like; water-soluble amine addition salts such as ammonium salts, N-methylglucaminates and the like; lower alkanol ammonium salts; and salts derived from the other pharmaceutically acceptable organic amine bases.

A therapeutic agent and a composition for neuropathic pain according to the present invention are effective for treating neuropathic pain. Examples of the neuropathic pain include neuropathic pains in postherpetic neuralgia, trigeminal neuralgia, diabetic neuralgia, cancer pain, persistent postoperative or posttraumatic pain, hyperalgia, allodynia, postthoracotomy pain, CRPS, pain associated with multiple sclerosis, AIDS, thalamic pain, paraplegic pain caused by myelopathy, anesthesia dolorosa, phantom limb pain and the like. A therapeutic agent for neuropathic pain according to the present invention is especially effective for treating hyperalgia and allodynia.

A therapeutic agent for neuropathic pain according to the present invention may be administered orally or parenterally with no specific limitation on the manner of administration. A peripheral benzodiazepine receptor antagonist as an active ingredient of the therapeutic agent for neuropathic pain according to the present invention may be provided independently, or provided as being contained in a formulation together with a pharmaceutically acceptable carrier or a pharmaceutical additive. In the latter case, the peripheral benzodiazepine receptor antagonist as an active ingredient of the present invention may be contained in, for example, 0.1 to 99.9% by weight with respect to the entirety of the formulation.

Examples of the pharmaceutically acceptable carrier or additive usable in the present invention include excipient, disintegrator, binder, lubricant, coating agent, colorant, diluent, dissolving agent, dissolution aid, tonicity agent, pH modifier, stabilizer, and the like.

Examples of the form of formulation suitable to oral administration include powder, tablet, capsule, fine granule, granule, liquid, syrup and the like. For oral administration, any of various excipients such as microcrystalline cellulose, sodium citrate, calcium carbonate, dipotassium phosphate, glycine and the like may be used together with any of various disintegrators such as starch (preferably corn, potato or tapioca starch), alginic acid, a certain type of silicate double salt and the like; and a granule-forming binder such as polyvinylpyrrolidone, sucrose, gelatin, gum arabic or the like. A lubricant such as magnesium stearate, sodium lauryl sulfate, talc or the like is often very effective for tablet formation. A gelatin capsule filled with the same type of solid composition may be used. Substances preferably usable in connection with this include lactose as well as high-molecular-weight polyethyleneglycol. For preparing an aqueous suspension and/or elixir for oral administration, the active ingredient may be used together with any of various types of sweeteners, flavorings, coloring agents or dyes, optionally an emulsifier and/or a suspending agent, as well as a diluent such as water, ethanol, propyleneglycerol, glycerol, or the like or a combination thereof.

Examples of the form of formulation suitable to parenteral administration include injection, suppository and the like. For parenteral administration, the active ingredient of the present invention may be dissolved in either sesame oil or peanut oil, or in an aqueous solution of propyleneglycol. When necessary, the aqueous solution is appropriately buffered (preferably to pH 8 or higher) to first isotonize the liquid diluent. Such an aqueous solution is suitable for intravenous injection, and an oleaginous solution is suitable for intraarticular injection, intramuscular injection and subcutaneous injection. All of these solutions can easily be produced under aseptic conditions by a standard pharmaceutical technology well known to those skilled in the art. In addition, the active ingredient of the present invention may be topically administered to skin or the like. In such a case, it is desirable to topically administer the active ingredient in the form of cream, jelly, paste or ointment in accordance with the standard pharmaceutical practice.

A therapeutic agent for neurophathic pain according to the present invention may be administered in an appropriate dose, with no specific limitation, which is selected in accordance with various conditions including the type of pain, age or symptom of the patient, administration route, purpose of treatment, and presence or absence of another medication used together with the agent. A daily dose of the therapeutic agent for neuropathic pain according to the present invention is, for example, about 50 to about 8,000 mg, and preferably 100 to 2000 mg, for an adult (e.g., body weight: 60 kg). When administered as an injection, a daily dose is about 100 to about 5,000 mg, and preferably 180 to 1,800 mg, for an adult (e.g., body weight: 60 kg). Such a daily dose may be divided into 2 to 4 separate doses.

EXAMPLES

Hereinafter, the present invention will be described more specifically by way of examples, which are not intended to limit the scope of the present invention.

(Experimental Materials and General Experimental Method)

(1) Model Animals

As experimental animals, neuropathic pain model rats obtained by conducting complete ligation on L5/L6 spinal nerves of 6-week-old male rats (body weight: 198.5 to 223.8 g) were used.

(2) Grouping

Mechanical stimulation tests were carried out using Dynamic Plantar Aesthesiometer (37400, Ugo Basile), and thermal stimulation tests were carried out using a plantar thermal stimulation tester (Plantar Test 7370, Ugo Basile). The pain threshold of the feet of each model animal was measured, and the animals were divided into groups such that the pain thresholds are uniform among the groups as measured prior to administration on each day of the experiment. In mechanical stimulation, model animals exhibiting a foot pain threshold of 8.0 g or more were excluded from the tests. In thermal stimulation, model animals exhibiting a pain threshold of 10 seconds or more were excluded from the tests.

(3) Preparation of Test Substance

The test substance was prepared as follows. The base material was ground with an agate mortar and a pestle, and 0.5 w/v % carboxymethylcellulose sodium (CMC-Na) as a medium was gradually added thereto to form a uniform suspension. The concentration of the liquid to be administered was adjusted (to 0.06, 0.6 and 6.0 mg/ml liquid) with a graduated cylinder or a volumetric flask, only before use.

(4) Method of Administration

The test substance is administered for the purpose of ascertaining the direct effect on spinal cord. Since the test substance had been confirmed to pass through the brain barrier, a simple intraperitoneal administration was used. The test substance in a volume of 5 ml/kg was intraperitoneally administered using a syringe barrel and a needle.

Example 1

Mechanical Stimulation Method

Groups each including five neuropathic pain model male rats (341.7 to 416.8 g) were used. Before administration of PK11195, and at 30 minutes, 60 minutes and 90 minutes after administration of PK11195, the pain threshold of the left plantar of each rat was measured using a stimulating apparatus which had been set such that the maximum pressure would be 15.0 g and the maximum pressure would be reached in 20 seconds. The results are shown in FIG. 1. In FIG. 1, "**" indicates that there is a significant difference at P<0.01 based on the Dunnett's multiple comparison test, and "*" indicates that there is a significant difference at P<0.05 based on the Dunnett's multiple comparison test (this is also applied to FIG. 2).

As shown in FIG. 1, the control group to which physiological saline was administered exhibited a maximum pain threshold of 7.0 g after the administration, whereas the group to which PK11195 was administered exhibited the following results: (a) after the administration of 0.3 mg/kg, the maximum pain threshold was 7.7 g; (b) after the administration of 3 mg/kg, the maximum pain threshold was 9.6 g; and (c) after the administration of 30 mg/kg, the maximum pain threshold was 10.4 g. As understood from these results, PK11195 significantly increased the pain threshold when administered in the amounts of 3 mg and 30 mg. This confirmed the analgesic effect of PK11195 on neuropathic pain. In the above-described neuropathic pain model rats, the pain threshold was lowered conspicuously due to allodynia, by which tactile stimulus which is not usually felt as pain is felt as pain. Then, PK11195 increased the pain threshold when intraperitoneally administered and was confirmed to improve the symptom of allodynia.

Example 2

Thermal Stimulation Method

Groups each including five neuropathic pain model male rats (371.0 to 454.2 g) were used. Before administration of PK11195, and at 30 minutes, 60 minutes and 90 minutes after administration of PK11195, the pain threshold of the left plantar of each rat was measured using a plantar stimulating apparatus set to a thermal stimulation intensity of 35. The results are shown in FIG. 2.

Figure 2:
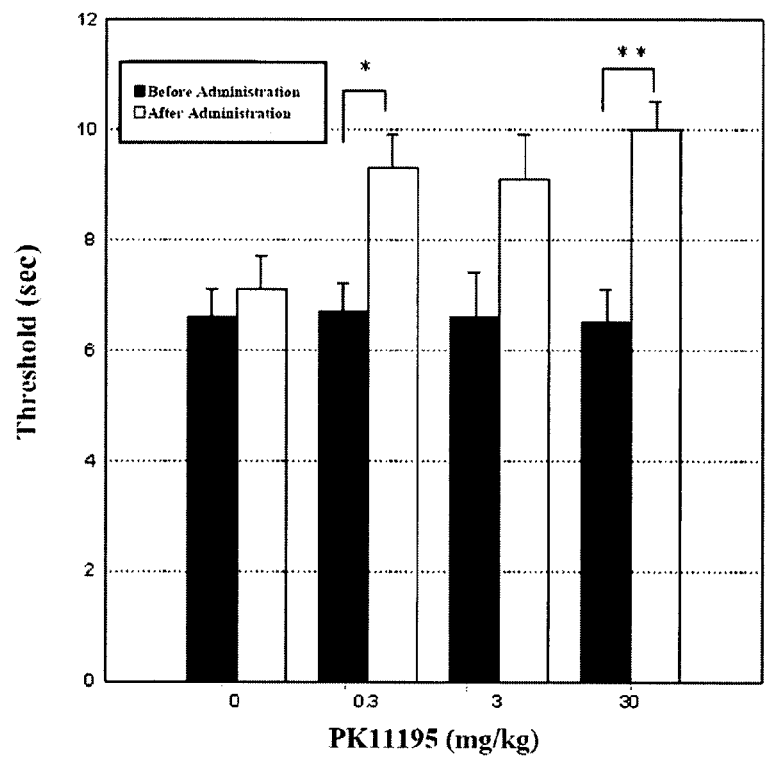
FIG. 2 shows experimental results in Example 2, illustrating a change in the pain threshold against thermal stimulation exhibited by rats after PK11195 was intraperitoneally administered to the rats having neuropathic pain due to nerve injury.

As shown in FIG. 2, the control group to which physiological saline was administered exhibited a maximum pain threshold of 7.1 seconds after the administration, whereas the group to which PK11195 was administered exhibited the following results: (a) after the administration of 0.3 mg/kg, the maximum pain threshold was 9.3 seconds; (b) after the administration of 3 mg/kg, the maximum pain threshold was 9.1 seconds; and (c) after the administration of 30 mg/kg, the maximum pain threshold was 10.0 seconds. As understood from these results, PK11195 significantly increased the pain threshold when administered in the amounts of 0.3 mg and 30 mg. This confirmed the analgesic effect of PK11195 on neuropathic pain. The administration of 3 mg/kg did not exhibit a statistically significant difference, but still increased the pain threshold and is considered to have a mild analgesic effect.

(Discussion)

The above-described examples clarified that a peripheral benzodiazepine receptor (PBR) antagonist is effective for treating neuropathic pain.

INDUSTRIAL APPLICABILITY

As described above, a therapeutic agent for neuropathic pain according to the present invention which comprises a peripheral benzodiazepine receptor antagonist has an action of improving symptoms of neuropathic pain occurred by various causes, and is effectively usable for treatment of neuropathic pain.

The invention claimed is:

1. A method for treating neuropathic pain by administering an effective amount of a peripheral benzodiazepine receptor antagonist to a mammal in need thereof.

2. The method of claim 1, wherein the peripheral benzodiazepine receptor antagonist is selected from 1-(2-chlorophenyl)-N-methyl-N-(1-methylpropyl)-3-isoquinolinecarboxyamide; (−)-N,N-dimethyl-2-methyl-3-[4-(2-phenyl)quinolinyl]propaneamide; (+)-N,N-dimethyl-2-methyl-3-[4-(2-phenyl)quinolinyl]propaneamide; 1-(2-fluoro-5-nitrophenyl)-N-methyl-N-(1-methylpropyl)-3-isoquinolinecarboxyamide; 7-chloro-N,N,5-trimethyl-4-oxo-3-phenyl-3,5-dihydro-4H-pyridazino-[4,5-b]indole-1-acetoamide; and pharmaceutically acceptable salts thereof.

3. The method of claim 1, wherein the peripheral benzodiazepine receptor antagonist is 1-(2-chlorophenyl)-N-methyl-N-(1-methylpropyl)-3-isoquinolinecarboxyamide or a pharmaceutically acceptable salt thereof.

4. The method of claim 1, wherein the neuropathic pain is at least one symptom selected from neuropathic pains in postherpetic neuralgia, trigeminal neuralgia, diabetic neuralgia, cancer pain, persistent postoperative or posttraumatic pain, hyperalgia, allodynia, postthoracotomy pain, CRPS, pain associated with multiple sclerosis, AIDS, thalamic pain, paraplegic pain caused by myelopathy, anesthesia dolorosa and phantom limb pain.

* * * * *